United States Patent [19]
Kanto et al.

[11] Patent Number: 5,286,705
[45] Date of Patent: Feb. 15, 1994

[54] HEAT TRANSFER SHEET

[75] Inventors: Jumpei Kanto; Hitoshi Saito; Masayuki Nakamura; Yasushi Sato, all of Tokyo, Japan

[73] Assignee: Dai Nippon Insatsu Kabushiki Kaisha, Japan

[21] Appl. No.: 474,052

[22] PCT Filed: Aug. 29, 1989

[86] PCT No.: PCT/JP89/00877
§ 371 Date: Apr. 30, 1990
§ 102(e) Date: Apr. 30, 1990

[87] PCT Pub. No.: WO90/02047
PCT Pub. Date: Mar. 8, 1990

[30] Foreign Application Priority Data

Aug. 29, 1988 [JP] Japan .................. 63-212397
Dec. 27, 1988 [JP] Japan .................. 63-327883

[51] Int. Cl.$^5$ .................. B41M 5/035; B41M 5/38
[52] U.S. Cl. .................. 503/227; 428/195; 428/913; 428/914
[58] Field of Search .................. 8/471; 428/195, 913, 428/914; 503/227

[56] References Cited

U.S. PATENT DOCUMENTS 5,077,264  12/1991  Hayashi et al. .................. 503/227

FOREIGN PATENT DOCUMENTS

| 216483 | 4/1987 | European Pat. Off. | 503/227 |
| 423336 | 4/1991 | European Pat. Off. | 503/227 |
| 48-24811 | 3/1973 | Japan | 503/227 |
| 48-42278 | 12/1973 | Japan | 503/227 |
| 45-130390 | 12/1973 | Japan | 503/227 |
| 61-268494 | 11/1986 | Japan | 503/227 |
| 1-263082 | 10/1989 | Japan | 503/227 |
| 2159971 | 12/1985 | United Kingdom | 503/227 |

OTHER PUBLICATIONS

Patent Abstracts of Japan, vol. 14, No. 23 (M-920)(3966) Jan. 17, 1990, & JP-A-01 263082 (Mitsubishi Kasei Corporation) Oct. 19, 1989.

*Primary Examiner*—B. Hamilton Hess
*Attorney, Agent, or Firm*—Parkhurst, Wendel & Rossi

[57] ABSTRACT

A heat transfer sheet according to the present invention includes a substrate sheet and a dye carrying layer formed on its one major side, and is characterized in that a dye included in the dye carrying layer is expressed by the following general formula (I) or (II):

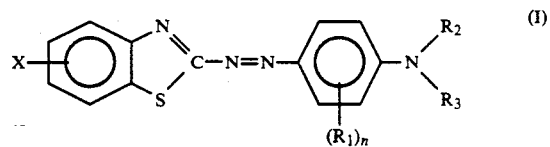

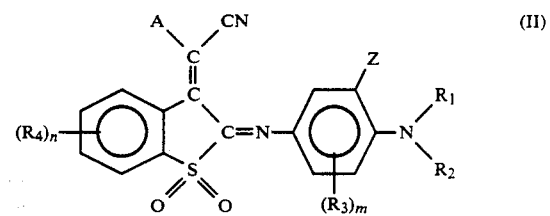

An image formed with such a heat transfer sheet shows excellent fastness properties, and excels in resistance to contamination in particular.

4 Claims, No Drawings

HEAT TRANSFER SHEET

TECHNICAL FIELD

The present invention relates to a heat transfer sheet and, more particularly, to a heat transfer sheet capable of easily providing a recording image excelling in various fastness properties.

BACKGROUND ART

Heretofore, various heat transfer techniques have been known in the art, including sublimation type transfer systems wherein a sublimable dye is carried on a substrate sheet such as paper to make a heat transfer sheet, which is then overlaid on an imageable material (image-receiving material), for instance, a woven fabric made of polyester to apply heat energy in the form of a pattern from the back side of the heat transfer sheet, thereby transferring the sublimable dye into the imageable material.

With a sublimation textile printing system of the above sublimation transfer systems, in which the imageable material used is made of, e.g., a polyester textile, relatively satisfactory dye transfer is achieved, since heat energy is applied over a relatively extended period of time so that the imageable material per se can be heated by that heat energy.

With an advance in recording techniques, however, fine characters or figures or photographic images could have been formed at high speeds on imageable materials made of, e.g., polyester or paper sheets having thereon a dye-receiving layer by means of a thermal head, etc. In this case, the application of thermal energy is required to be achieved within a time as short as fractions of a second. However, no image of sufficient density can be obtained, since the sublimable dyes and imageable materials are not well heated within such a short time.

In order to cope with such high-speed recording, sublimable dyes excelling in sublimability have thus been developed. However, problems with such dyes of excellent sublimability are that after transfer, they transfer into the imageable materials or bleed onto their surfaces with time, generally because of their low molecular weight. In consequence, the images, once formed, become out of order or blurred, or otherwise contaminate surrounding articles.

In the art of heat transfer using sublimable dyes, there is thus still strong demand for the development of a heat transfer sheet which provides a clear image of sufficient density by the application of thermal energy within such short a time as mentioned above and imparts improved fastness properties to the formed image.

It is therefore an object of the present invention to satisfy the above demand.

DISCLOSURE OF THE INVENTION

Thus, the present invention provides a heat transfer sheet comprising a substrate sheet and a dye carrying layer formed on its one major side, characterized in that a dye included in said dye carrying layer is expressed by the following general formula (I):

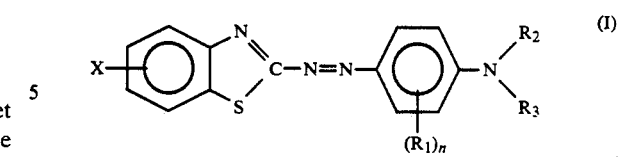

wherein:
$R_1$ stands for a hydrogen atom, a halogen atom or a substituent such as an alkyl, aryl, cycloalkyl, arylalkyl, alkoxy, acylamino or aminocarbonyl group which may include a substituent, n is 1 or 2, $R_2$ and $R_3$ each denote an alkyl group which may or may not include a substituent, or may form a ring together, and X indicates a hydrogen atom or at least one substituent.

According to another aspect of the present invention, there is provided a heat transfer sheet comprising a substrate sheet and a dye carrying layer formed on its major side, characterized in that a dye included in said dye carrying layer is expressed by the following general formula (II):

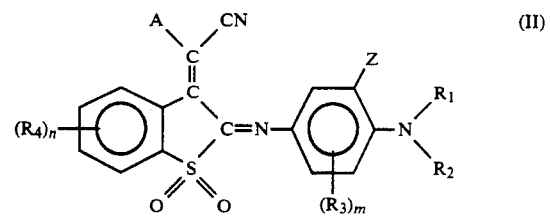

wherein:
A stands for a cyano, alkoxycarbonyl, aryloxycarbonyl, carbamoyl, alkylcarbamoyl, arylcarbamoyl, alkylcarbonyl, arylcarbonyl, alkylsulfonyl, alkylsulfonylamino, arylsulfonyl or aryl group, $R_1$ denotes a substituted or unsubstituted alkyl, aralkyl or aryl group, or an atom or atomic group which form a five- or six-membered ring together with Z, $R_2$ indicates a substituted or unsubstituted alkyl, aralkyl or aryl group, said $R_1$ and $R_2$ may form a five- or six-membered ring which may include an oxygen or nitrogen atom, $R_3$ stands for a hydrogen or halogen atom or an alkyl, alkoxy or acylamino group which may include a substituent, $R_4$ denotes a hydrogen or halogen atom or an alkyl, alkoxy, nitro, cyano, acylamino or aryl group which may include a substituent, Z indicates a hydrogen atom or an atom or atomic group which forms a five- or six-membered ring together with $R_1$, and n and m each are 1 or 2.

Studies of the present inventors have revealed that it is an essential condition for conventional sublimation textile printing techniques using textiles or woven fabrics of polyester, etc. that the dye used is sublimable or vaporizable (i.e., has the property of being capable of transferring through a space present between a heat transfer sheet and a woven fabric), since the heat transfer sheet is unlikely to come into close contact with the woven fabric that is an imageable material due to the surface of the latter lacking smoothness. In the case of using as an imageable material a polyester sheet or surface-processed paper having a plain surface, etc., however, it has now been found that as the heat transfer sheet is brought into full contact with the imageable material at the time of heat transfer, what is of crucial importance is not only the sublimability and vaporizability but also the property of the dye that it can travel thermally across the interface between the two brought into close contact with each other, and that such a property is greatly affected by the chemical structure of the dye used, what substituent it has, or where that substituent is located. This leads to another finding that with selected dyes of suitable molecular structures, even if they have a molecular weight so high that they are considered unusable from a common sense standpoint, good thermal transfer is achievable. It has thus been found that by using a heat transfer sheet carrying such a dye, it is possible to make a record of an image of high density and improved fastness properties even with the application of thermal energy within a very short time, since the dye used transfers easily into an imageable material.

BEST MODE FOR CARRYING OUT THE INVENTION

The present invention will now be explained in more detail with reference to the preferred embodiments.

The dye used in the first aspect of the present invention may be prepared by the known coupling reaction of ziazonium compounds of 2-aminobenzothiazole or their derivatives with couplers such as N,N-dialkylanilines or their derivatives.

Of the thus prepared dyes according to the present invention, particular preference is given to those of the general formula (I) in which $R_1$ is a hydrogen atom or an alkoxy group such as methoxy, ethoxy, propoxy or butoxy, located at the 2-position with respect to the azo group, and $R_2$ and $R_3$ each are a $C_1$-$C_{20}$ alkyl group such as methyl, ethyl, propyl, butyl, pentyl, hexyl, heptyl, octyl, nonyl, decyl, undecyl, dodecyl or hexadecyl, which may include a polar substituent such as a hydroxyl, amino, alkylamino, acylamino, sulfonylamino, aminocarbonyl, aminosulfonyl, alkoxycarbonyl, alkoxysulfonyl, cyano, alkoxy, phenyl, cycloalkyl or nitro group or a halogen atom, and X is a hydrogen atom or an alkoxy group such as methoxy, ethoxy, propoxy or butoxy, located at the 6-position, and which have a selected molecular weight of at least 320, preferably at least 350. By far the most preference is given to dyes of the general formula (I) wherein at least one of $R_1$ and X is a lower alkoxy group and at least one of $R_2$ and $R_3$ is an alkyl group having 1 to 20 carbon atoms, which is substituted by a hydroxyl or cyano group.

By detailed studies of the present inventors, the dyes of the general formula (I) have their molecular weight increased to at least 320 or at least 350 by selecting for $R_1$-$R_3$ and X groups other than hydrogen, e.g., substituted or unsubstituted alkyl groups, etc. Unlike generally well-established conceptions, however, it has now been found that the dyes having the above general formula are likely to decrease in their melting points, and that when such dyes are used as the dyes for heat transfer sheets, they transfer from the heat transfer sheets to imageable materials at an increased rate, even though they are heated by a thermal head, etc., within a very short time, and provide images improved in terms of fastness, esp., storability and light resistance.

With thiazole dyes coming under the general formula (I) but having a molecular weight below 300, on the other hand, it has been found that the resulting images are satisfactory in the density of developed color, etc., but are not in terms of storability and light resistance.

In addition, it has been found that the above preferable dyes are so improved in their solubility in general-purpose organic solvents used for the preparation of heat transfer sheets such as, for instance, methyl ethyl ketone, toluene, ethanol, isopropyl alcohol, cyclohexanone, ethyl acetate or their mixed solvents that they can be present on dye carrying layers formed on the heat transfer sheets in a non- or low-crystalline state, and so can easily transfer thermally into imageable materials in the quantity of heat applied that is much lower than that required in such a high-crystalline state as encountered with conventional dyes.

Illustrative dyes suitable for the present invention will now be summarized in Table A1 showing illustrative examples of the substituents $R_1$-$R_3$, n and X in the general formula (I).

TABLE A1

| No. | X | n | $R_1$ | $R_2$ | $R_3$ |
|---|---|---|---|---|---|
| 1 | $CH_3$ | 1 | H | $C_2H_5$ | $C_2H_5$ |
| 2 | $CH_3$ | 1 | $OC_2H_5$ | $C_2H_4CN$ | $C_2H_5$ |
| 3 | $CH_3$ | 2 | $CH_3$ | $C_2H_4NHSO_2CH_3$ | $C_2H_5$ |
| 4 | $OCH_3$ | 1 | H | $C_2H_5$ | $C_2H_5$ |
| 5 | $OC_2H_5$ | 1 | $OC_2H_5$ | $C_2H_5$ | $C_2H_5$ |
| 6 | $OC_2H_5$ | 2 | $OC_2H_5$ | $C_2H_4OH$ | $C_2H_5$ |
| 7 | $OC_2H_5$ | 1 | H | $C_2H_4CN$ | $CH_3$ |
| 8 | $OC_2H_5$ | 1 | $NHCOCH_3$ | $C_2H_5$ | $C_2H_5$ |
| 9 | $NO_2$ | 1 | H | $C_2H_5$ | $C_2H_5$ |
| 10 | $NO_2$ | 2 | $CH_3$ | $C_2H_5$ | $C_2H_5$ |
| 11 | $NO_2$ | 1 | * | $C_2H_5$ | $CH_3$ |
| 12 | Cl | 2 | $OC_2H_5$ | $C_2H_5$ | $C_2H_5$ |
| 13 | Cl | 1 | H | —$C_2H_4OC_2H_4$— | |
| 14 | Cl | 1 | $CH_3$ | $C_2H_5$ | $C_2H_5$ |
| 15 | $CH_2CN$ | 1 | $CH_3$ | $C_2H_5$ | $C_2H_5$ |
| 16 | $N(CH_3)_2$ | 2 | $OC_2H_5$ | $C_2H_4OH$ | $C_2H_5$ |
| 17 | $CH=CHCH_3$ | 1 | $CH_3$ | $C_2H_4OCH_3$ | $C_2H_5$ |
| 18 | iso-$C_3H_7$ | 2 | $CH_3$ | $CH_3$ | $CH_3$ |
| 19 | H | 1 | $OC_2H_5$ | $C_8H_{17}$ | $C_8H_{17}$ |
| 20 | H | 1 | $CH_3$ | $C_2H_4Ph$ | H |
| 21 | Br | 1 | $C_4H_9$ | $C_8H_{17}$ | $C_8H_{17}$ |
| 22 | $NHCOCH_3$ | 1 | iso-$C_3H_7$ | $C_2H_4OH$ | $C_2H_5$ |
| 23 | $CH_3$ | 1 | $NHSO_2CH_3$ | $C_2H_5$ | $C_2H_4OH$ |

*—CH=CH—CH=CH-group forming a naphthalene ring.

The second aspect of the present invention will then be explained.

The dyes used according to the second aspect of the present invention are well-known in themselves, and may be easily prepared by the condensation-with-dehydration of dihydrobenzothiophene-1,1-dioxide derivatives expressed by the following general formula (III) with nitroso compounds expressed by the following general formula (IV) in the presence of solvents.

such as hydroxyl, amino, alkylamino, acylamino, sulfonylamino, aminocarbonyl, aminosulfonyl, alkoxycarbonyl, alkoxysulfonyl, cyano, alkoxy, phenyl, cycloalkyl or nitro group or a halogen atom.

Illustrative dyes suitable for the present invention will now be summarized in Table B1 showing illustrative examples of the substituents $R_1$-$R_4$, A and Z, m and n in the general formula (II) as well as their molecular weight.

TABLE B1

| No. | Z | $R_1$ | $R_2$ | m | $R_3$ | n | $R_4$ | A | Molecular Weight |
|-----|---|-------|-------|---|-------|---|-------|---|------------------|
| 1 | H | $C_2H_5$ | $C_2H_5$ | 1 | $OC_2H_5$ | 1 | H | CN | 434 |
| 2 | H | $C_2H_5$ | $C_2H_4OH$ | 1 | $CH_3$ | 1 | H | CN | 420 |
| 3 | H | $C_2H_5$ | $C_2H_5$ | 2 | $OC_2H_5$ | 1 | H | CN | 478 |
| 4 | H | $CH_3$ | Ph | 1 | Cl | 1 | $NO_2$ | CN | 503.5 |
| 5 | H | $C_2H_5$ | $C_2H_4Cl$ | 1 | $CH_3$ | 1 | $NHCOCH_3$ | CN | 495.5 |
| 6 | $CHCH_3$ | $CH_2C(CH_3)_2$*1 | $C_2H_5$ | 1 | $CH_3$ | 1 | H | CN | 458 |
| 7 | H | $C_6H_{13}$ | $C_6H_{13}$ | 1 | $NHSO_2CH_3$ | 1 | H | CN | 596 |
| 8 | H | *2 | $C_2H_5$ | 1 | H | 1 | $OC_2H_5$ | CN | 515 |
| 9 | H | $C_2H_5$ | $C_2H_4OH$ | 1 | $OC_2H_5$ | 1 | H | CN | 450 |
| 10 | H | $C_2H_5$ | $C_2H_5$ | 2 | $CH_3$ | 1 | CN | CN | 444 |
| 11 | H | $C_2H_5$ | $CH_2Ph$ | 1 | H | 1 | H | CN | 452 |
| 12 | H | $C_2H_5$ | $C_2H_4CN$ | 1 | $NHCOCH_3$ | 1 | Cl | CN | 506.5 |
| 13 | H | $CH_3$ | $C_2H_5$ | 1 | $CH_3$ | 1 | H | CN | 404 |
| 14 | H | $(CH_2)_5$*3 | | 1 | $CH_3$ | 1 | H | $COOCH_3$ | 463 |
| 15 | H | $C_2H_5$ | $C_2H_5$ | 1 | $CH_3$ | 1 | H | $COOCH_3$ | 437 |
| 16 | H | $C_2H_5$ | $C_2H_5$ | 1 | $CH_3$ | 2 | CN | $COOCH_3$ | 487 |
| 17 | H | $C_2H_5$ | $C_2H_4OH$ | 1 | $C_4H_9$ | 1 | $CH_3$ | $COOC_2H_5$ | 524 |
| 18 | H | $C_2H_5$ | $C_2H_5$ | 1 | $OC_2H_5$ | 1 | Cl | $COOC_2H_5$ | 480 |
| 19 | H | $C_2H_5$ | $C_2H_5$ | 1 | $CH_3$ | 1 | H | COPh | 483 |
| 20 | H | $C_2H_4OH$ | $C_2H_5$ | 1 | CH | 1 | H | $CONHC_3H_7$ | 480 |
| 21 | H | $C_2H_4OH$ | $C_2H_5$ | 1 | $CH_3$ | 1 | H | CONHPh | 514 |
| 22 | H | $C_2H_5$ | $C_2H_5$ | 1 | $CH_3$ | 1 | H | $NHSO_2CH_3$ | 472 |
| 23 | H | $C_2H_4OH$ | $C_2H_5$ | 1 | $CH_3$ | 1 | H | Ph | 471 |

*1 Z forms a ring with $R_1$.
*2: $C_2H_4NHSO_2CH_3$
*3 Z forms a ring with $R_1$.

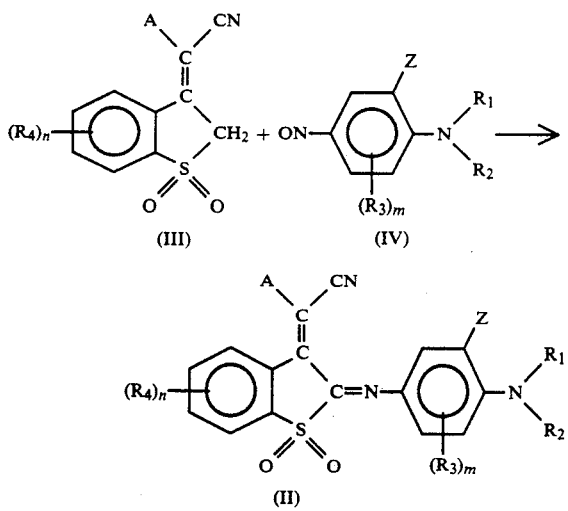

wherein $R_1$-$R_5$, X and Z have the same meanings as defined above.

In the second aspect of the present invention, preference is given to dyes which have a molecular weight of 400 or more, and in which the substituent Z is a hydrogen atom, $R_1$ and/or $R_2$ are an ethyl group which may have a hydroxyl group, $R_3$ is an alkyl or alkoxy group located at the ortho-position with respect to the azomethyne group, $R_4$ is a hydrogen atom, A is a cyano or alkoxycarbonyl group and m and n are both 1.

Preference is also given to dyes in which at least one of the substituents $R_1$-$R_4$ and A includes a polar group The heat transfer sheets according to the present invention are characterized in that such specific dyes as mentioned above are used, and may otherwise be identical with conventional known heat transfer sheets.

As the substrate sheets used for the heat transfer sheets containing the above dyes according to the present invention, use may be made of any known material having some heat resistance and strength. By way of example alone, use may be made of paper sheets, various-processed paper sheets, polyester films, polystyrene films, polypropylene films, polysulfone films, polycarbonate films, aramide films, polyvinyl alcohol films, cellophane and so on, all having a thickness of about 0.5 to 50 μm, preferably about 3 to 10 μm. Particular preference is given to polyester films.

The dye carrying layers formed on the surfaces of such substrate sheets as mentioned above may be obtained by carrying the dyes of the general formula (I) or (II) on any suitable binder resin.

As the binder resins to carry thereon the above dyes, use may be made of any known resin. Preferable to this end are cellulosic resins such as ethyl cellulose, hydroxyethyl cellulose, ethylhydroxy cellulose, hydroxypropyl cellulose, methyl cellulose, cellulose acetate and cellulose acetate butyrate; and vinylic resins such as polyvinyl alcohol, polyvinyl acetate, polyvinyl butyral, polyvinyl acetal, polyvinyl pyrrolidone and polyacrylic amide. Of these resins, particular preference is given to polyvinyl butyral and polyvinyl acetal in view of heat resistance and dye-transfer properties.

The dye carrying layers of the heat transfer sheets according to the present invention are basically formed of the above materials and, if required, may include various additives such as those heretofore known in the art.

Preferably, such a dye carrying layer may be formed on the above substrate sheet by dissolving or dispersing the above dye, binder resin and any other components in a suitable solvent to prepare a coating or ink liquid for the formation of the dye carrying layer and, then, coating it on the substrate, followed by drying.

Suitably, the carrying layer formed in this manner has a thickness of about 0.2 to 5.0 μm, preferably about 0.4 to 2.0 μm and a dye content of 5 to 70% by weight, preferably 10 to 60% by weight based on the weight thereof.

The heat transfer sheets of the present invention may be successfully used as such for the purpose of heat transfer. By the provision of an anti-tack layer, i.e., a release coat on the surface of the dye carrying layer, however, it is possible to prevent the heat transfer sheet from sticking to an imageable material at the time of heat transfer and hence use a much more increased heat transfer temperature, thereby forming an image of much more improved density.

Some anti-tack effect may be obtained by using only anti-tack inorganic powders for that release layer. However, more preferable results are obtained by forming a release layer of 0.01 to 5 μm, preferably 0.05 to 2 μm in thickness from a resin having excellent releasability such as silicone polymers, acrylic polymers and fluorinated polymers.

It is understood that such inorganic powders or releasable polymers as mentioned above produce a sufficient release effect, even if they are contained in the dye carrying layer.

Further, such a heat transfer sheet may additionally be provided on its back side with a heat-resistant layer so as to prevent the heat of a thermal head from having an adverse influence thereon.

The imageable material used for forming an image with such a heat transfer sheet as mentioned above may be any material having its recording surface capable of receiving the above dye. In the case of paper, metal, glass, synthetic resin or the like having the property of being incapable of receiving the dye, they may be provided on one of their major surfaces with a dye receiving layer.

As the imageable materials which may not contain any dye receiving layer, use may be made of fibers, woven fabrics, films, sheets and formings formed of, for instance, polyolefinic resins such as polypropylene, halogenated polymers such as polyvinyl chloride and polyvinylidene chloride, vinylic polymers such as polyvinyl acetate and polyacrylic esters, polyester resins such as polyethylene terephthalate and polybutylene terephthalate, polystyrene resins, polyamide resins, copolymeric resins of olefins such as ethylene and propylene with other vinylic monomers, ionomers, cellulosic resins such as cellulose diacetate and polycarbonate.

Particular preference is given to polyester sheets or films or processed paper having a polyester layer. Non-dyeable imageable materials such as paper, metal and glass may be formed into imageable materials by coating a solution or dispersion of such a dyeable resin as mentioned above on their recording surfaces, followed by drying, or laminating a film of such resins thereon.

As is the case with the above paper, such a dyeable imageable material may additionally be formed on its surface with a dye receiving layer of a resin of much more improved dyeability.

The dye receiving layer prepared in this manner may be formed of a single material or a plurality of materials. As a matter of course, it may contain various additives, provided that the desired object is achievable.

Such a dye receiving layer may have any suitable thickness but may generally be 3 to 50 μm in thickness. Although the dye receiving layer should preferably be provided in the form of a continuous coat, it may be provided in the form of a discontinuous coat by using a resin emulsion or dispersion.

The imageable material is basically as mentioned above and may successfully be used as such. However, this imageable material or its dye receiving layer may contain inorganic powders for anti-tack purposes. In this way, much more improved heat transfer is achievable, since the heat transfer sheet is prevented from sticking to the imageable material even at elevated heat transfer temperatures. By far the most preference is given to finely divided silica.

In place of or in combination with such inorganic powders as the above silica, such resins of improved releasability as already indicated may be added. By far the most preference is given to cured silicone compounds, typically, cured products comprising epoxy modified silicone oil and amino modified silicone oil. Such a release agent may preferably account for about 0.5 to 30% by weight of the dye receiving layer.

In addition, the imageable material used may be either deposited on the surface of its dye receiving layer with such inorganic powders as already indicated so as to better its anti-tack effect or provided thereon with a layer consisting of such a release agent of improved releasability as already indicated.

At a thickness of about 0.01 to 5 μm, such a release layer produces an effect so sufficient that much more improvements can be introduced in dye acceptability, while preventing any sticking of the dye receiving layer of the heat transfer sheet to the imageable layer.

As the thermal energy applying means used for carrying out heat transfer with such a heat transfer sheet of the present invention as already indicated and such an imageable material as already stated, any of conventional means hitherto known in the art may be used. For instance, the desired object is successfully achievable by the application of a heat energy of about 5 to 100 mJ/mm$^2$ for a controlled recording time with such recording equipment as a thermal printer (e.g., Video Printer VY-100 made by Hitachi Co., Ltd., Japan).

According to the present invention as detailed above, although the dye used for the heat transfer sheet of the present invention is much higher in molecular weight than sublimable dyes used for conventional heat transfer sheets (having a molecular weight of about 150 to 250), it shows improved thermal transferability and excellent dyeability and color developability with respect to the imageable material due to its specific structure and its having a substituent at a specific position. Moreover, it is unlikely to transfer through, or bleed on, the heat transfer sheet after transferring.

Thus, the image formed with the heat transfer sheet of the present invention is so high in its fastness properties and so particularly improved in its resistance to both transfer and contamination that it cannot possibly be blurred or contaminate other articles, thus making it possible to solve various problems of the prior art.

Especially in the case of the dyes of the general formula (I) wherein at least one of $R_1$-$R_3$ contains a polar group, or of the general formula (II) wherein at least one of $R_1$–$R_4$, A and Z contains a polar group, such fastness properties as mentioned above are much more improved. Such effects as excellent as never anticipated from the prior art become marked especially when the dye receiving portion of the imageable material is formed of such a material as polyester. This appears to be because the polar group-containing dye is fixed into the polyester for some unknown reasons, but probably through a certain correlation between it and the ester bond that forms a polar group in the polyester.

The present invention will now be explained more illustratively with reference to the following reference examples, examples and comparative examples. It is understood that unless otherwise stated, "parts" and "%" are given on weight basis and that the structural formulae of dyes are estimated ones.

REFERENCE EXAMPLE A1

Dissolved in a mixed solution of 20 ml of acetic acid and 50 ml of sulfuric acid are 18 g of 2-amino-6-methyl-benzothiazole, with further addition of 100 g of ice water.

While the obtained solution is cooled down to 5° C. or below, a solution of 5 g of sodium nitrite in 20 ml of water is slowly added thereto for diazotation. After stirring at 0° to 5° C. for a further 2 hours, a small amount of sulfamic acid is added to the solution, with subsequent filtration yielding a diazo solution.

On the other hand, 15 g of diethylaniline are dissolved in a mixed solution of 30 g of hydrochloric acid with 400 ml of water. While this solution is ice-cooled under agitation to 0° to 5° C., small portions of the above diazotated solution are added thereto for coupling. After the completion of the coupling reaction, the reaction product is neutralized with sodium carbonate, and the precipitates are filtrated, washed with water and dried. Thus, 28.5 g of a dye expressed by the following structural formula were obtained in the form of purplish red crystals.

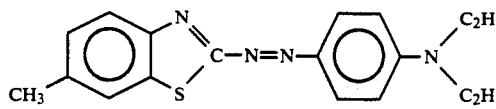

REFERENCE EXAMPLES A2 TO A22

Reference Example A1 was repeated with the 2-aminobenzothiazole derivatives and P-phenylenediamine derivatives corresponding to Nos. 2 to 23 in Table A1 to obtain the thiazole-azo dyes set forth in Table A1.

EXAMPLE A

Prepared was an ink composition for the formation of a dye carrying layer, composed of the following ingredients, which was then coated a 6-μm-thick polyethylene terephthalate film subjected to heat-resistant treatment on its back side in a quantity of 1.0 g/m² on dry basis. Subsequent drying gave the heat transfer sheets according to the present and comparative examples.

| | |
|---|---|
| Dyes set forth in Table A1 | 3 parts |
| Polyvinyl butyral resin | 4.5 parts |
| Methyl ethyl ketone | 46.25 parts |
| Toluene | 46.25 parts |

It is noted, however, that when the dyes were insoluble in the above composition, DMF, dioxane, chloroform, etc. were optionally used as the solvents.

Next, a coating solution composed of the following ingredients was coated on one side of a substrate sheet formed of synthetic paper (Yupo FPG #150 made by Oji Yuka Co., Ltd.) in an amount of 10.0 g/m² on dry basis, which was then dried at 100° C. for 30 minutes to obtain an imageable material.

| | |
|---|---|
| Polyester resin (Vylon 200 made by Toyobo Co., Ltd., Japan) | 11.5 parts |
| Vinyl chloride/vinyl acetate copolymer (VYHH made by UCC9 | 5.0 parts |
| Amino modified silicone (KF-393 made by the Shin-Etsu Chemical Co., Ltd., Japan) | 1.2 parts |
| Epoxy modified silicone (X-22-343 made by the Shin-Etsu Chemical Co., Ltd., Japan) | 1.2 parts |
| Methyl ethyl ketone/toluene/cyclohexanone (4:4:2 in weight ratio) | 102.0 parts |

Each of the above heat transfer sheets according to the present invention and comparative examples was overlaid on the above imageable material with the dye-carrying and dye-receiving layers located in opposition to each other. Then, recording was carried out from the back side of the heat transfer sheet with a thermal head under the following conditions: at a voltage of 10 V applied to the head for a printing time of 4.0 msec. The results are summarized in Table A2.

TABLE A2

| Dyes | Density of Development Color | Fastness | Light Resistance | Molecular Weight |
|---|---|---|---|---|
| 1 | 2.60 | Δ | ○ | 324 |
| 2 | 1.95 | ○ | ○ | 393 |
| 3 | 1.80 | ○ | ○ | 450 |
| 4 | 2.13 | Δ | ⊙ | 340 |
| 5 | 2.50 | ○ | ⊙ | 398 |
| 6 | 2.13 | ⊙ | ○ | 458 |
| 7 | 2.04 | ○ | ○ | 365 |
| 8 | 1.95 | ○ | ○ | 411 |
| 9 | 1.75 | ○ | ○ | 355 |
| 10 | 1.55 | ○ | ○ | 383 |
| 11 | 1.53 | ○ | ○ | 377 |
| 12 | 2.14 | ○ | ⊙ | 432.5 |
| 13 | 1.82 | ○ | ○ | 358.5 |
| 14 | 2.17 | ○ | ○ | 358.5 |
| 15 | 1.64 | ○ | ○ | 363 |
| 16 | 1.81 | ⊙ | ○ | 457 |
| 17 | 1.96 | ○ | ○ | 394 |
| 18 | 2.08 | ○ | ○ | 352 |
| 19 | 1.63 | ⊙ | ○ | 522 |
| 20 | 1.92 | ○ | ○ | 372 |
| 21 | 1.32 | ○ | ○ | 612.9 |
| 22 | 1.72 | ○ | ○ | 425 |
| 23 | 1.80 | ⊙ | ○ | 433 |

The hues of the dyes set forth in the above table are all red or purple.

COMPARATIVE EXAMPLES A1 TO A4

Example A1 was repeated, provided however that the dyes set forth in the following Table A3 were used in place of the dyes used therein. The results are shown in Table A3.

TABLE A3

| | Comparative Examples | | | |
|---|---|---|---|---|
| | A1 | A2 | A3 | A4 |
| Dyes | AI | AII | AIII | AIV |

TABLE A3-continued

|  | Comparative Examples | | | |
| --- | --- | --- | --- | --- |
|  | A1 | A2 | A3 | A4 |
| Density of Developed Color | 1.76 | 0.66 | 1.03 | 0.40 |
| Fastness | Δ | Δ | x | Δ |
| Light resistance | x | x | x | x |

Dye AI = Disperse red 1 (with a molecular weight of 314)
Dye AII = Disperse violet 1 (with a molecular weight of 238)
Dye AIII = Disperse violet 4 (with a molecular weight of 252)
Dye AIV = Disperse violet 28 (with a molecular weight of 305)

It is noted that the density of developed color as referred to above was measured with Densitometer RD-918 made by Macbeth Co., Ltd., U.S.A.

Storability was measured after the recorded images had been allowed to stand in an atmosphere of 50° C. for an extended period of time, and was estimated as follows.

Double circles indicate that the sharpness of the images underwent no change at all and that when the test pieces were rubbed with white paper, it was not altogether colored; circles indicate that the images lost sharpness with slight coloration of white paper; triangles indicate that the image lost sharpness with white paper being colored; and crosses indicate that the images became blurred with noticeable coloration of white paper.

Light resistance was measured according to JIS L 0842 and estimated as follows. Double circles indicate the test pieces having an initial fastness of 3 or more, as determined according to the secondary exposure method provided by JIS L 0841; circles indicate the test pieces having a value something of the order of 3; and crosses indicate the test pieces having a value below 3.

REFERENCE EXAMPLE B1

Dissolved in toluene were 1.2 parts of the nitroso compound expressed by the following structural formula:

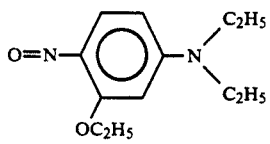

Then, a solution of 1.0 part of the dihydrobenzothiophene-1,1-dioxide derivative expressed by the following structural formula:

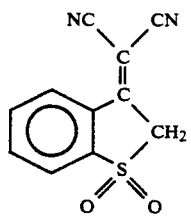

in toluene was added dropwise to the resulting solution under cooling conditions. After the completion of the dropwise addition, the reaction was continued for a further two hours. Afterwards, the precipitated crystals were filtrated for separation, and then recrystallized from ethyl acetate to obtain 0.7 parts of the dihydrobenzothiophene methyne dye expressed by the following structural formula:

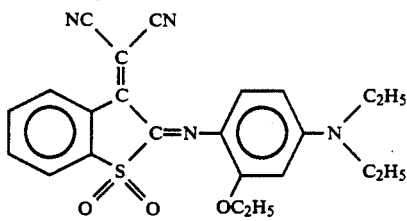

The maximum absorption wavelength (ethyl acetate) of said dye was found at 635 nm.

REFERENCE EXAMPLES B2 TO B22

With the nitroso compounds and dihydrobenzophenone-1,1-dioxide derivatives corresponding to Nos. 2 to 23 set forth in Table B1, Reference Example B1 was repeated to obtain the azomethyne dyes set forth in Table B1.

EXAMPLE B

Prepared was an ink composition for the formation of a dye carrying layer, composed of the following ingredients, which was then coated a 6-μm-thick polyethylene terephthalate film subjected to heat-resistant treatment on its back side in a quantity of 1.0 g/m² on dry basis. Subsequent drying gave the heat transfer sheets according to the present and comparative examples.

| Dyes set forth in Table B1 | 3 parts |
| --- | --- |
| Polyvinyl butyral resin | 4.5 parts |
| Methyl ethyl ketone | 46.25 parts |
| Toluene | 46.25 parts |

It is noted, however, that when the dyes were insoluble in the above composition, DMF, dioxane, chloroform, etc. were optionally used as the solvents.

Next, a coating solution composed of the following ingredients was coated on one side of a substrate sheet formed of synthetic paper (Yupo FPG #150 made by Oji Yuka Co , Ltd.) in an amount of 10.0 g/m² on dry basis, which was then dried at 100° C. for 30 minutes to obtain an imageable material.

| Polyester resin (Vylon 200 made by Toyobo Co., Ltd., Japan) | 11.5 parts |
| --- | --- |
| Vinyl chloride/vinyl acetate copolymer (VYHH made by UCC9 | 5.0 parts |
| Amino modified silicone (KF-393 made by the Shin-Etsu Chemical Co., Ltd., Japan) | 1.2 parts |
| Epoxy modified silicone (X-22-343 made by the Shin-Etsu Chemical Co., Ltd., Japan) | 1.2 parts |
| Methyl ethyl ketone/toluene/cyclohexanone (4:4:2 in weight ratio) | 102.0 parts |

Each of the above heat transfer sheets according to the present invention was overlaid on the above imageable material with the dye-carrying and dye-receiving layers located in opposition to each other. Then, recording was carried out from the back side of the heat transfer sheet with a thermal head under the following conditions: at a voltage of 10 V applied to the head for a printing time of 4.0 msec. The results are summarized in Table B2.

TABLE B2

| Dyes | Density of Development Color | Fastness | Hue |
|---|---|---|---|
| 1 | 1.85 | ○ | Indigo |
| 2 | 1.75 | ⊙ | Indigo |
| 3 | 1.80 | ○ | Indigo |
| 4 | 1.60 | ⊙ | Indigo |
| 5 | 1.70 | ⊙ | Indigo |
| 6 | 1.75 | ⊙ | Indigo |
| 7 | 1.45 | ⊙ | Indigo |
| 8 | 1.80 | ○ | Indigo |
| 9 | 1.70 | ⊙ | Indigo |
| 10 | 1.90 | ○ | Indigo |
| 11 | 1.80 | ⊙ | Indigo |
| 12 | 1.65 | ○ | Indigo |
| 13 | 2.10 | ○ | Indigo |
| 14 | 1.80 | ○ | Indigo |
| 15 | 2.05 | ○ | Indigo |
| 16 | 1.80 | ○ | Indigo |
| 17 | 1.60 | ⊙ | Indigo |
| 18 | 1.65 | ○ | Indigo |
| 19 | 1.70 | ○ | Indigo |
| 20 | 1.90 | ⊙ | Indigo |
| 21 | 1.55 | ⊙ | Indigo |
| 22 | 1.80 | ○ | Indigo |
| 23 | 1.80 | ⊙ | Indigo |

COMPARATIVE EXAMPLES B1 to B4

Example B1 was repeated, provided however that the dyes set forth in the following Table B3 were used in place of the dyes used therein. The results are shown in Table B3.

TABLE B3

| Comp. Ex. | Density of Developed Color | Fastness | Hue |
|---|---|---|---|
| B1 | 0.99 | x | Indigo |
| B2 | 1.16 | Δ | Indigo |
| B3 | 2.07 | x | Indigo |
| B4 | 1.12 | Δ | Indigo |
| B5 | 1.02 | x | Purple |

B1: Disperse blue 14
B2: Disperse blue 134
B3: Solvent blue 63
B4: Disperse blue 26
B5: Disperse violet 4

It is noted that the density of developed color as referred to above was measured with Densitometer RD-918 made by Macbeth Co., Ltd. U.S.A.

Storability was measured after the recorded images had been allowed to stand in an atmosphere of 50° C. for an extended period of time, and was estimated as follows.

Double circles indicate that the sharpness of the images underwent no change at all and that when the test pieces were rubbed with white paper, it was not altogether colored; circles indicate that the images lost sharpness with slight coloration of white paper; triangles indicate that the images lost sharpness with white paper being colored; and crosses indicate that the images became blurred with noticeable coloration of white paper.

Light resistance was measured according to JIS L 0842 and estimated as follows. Double circles indicate the test pieces having an initial fastness of 3 or more, as determined according to the secondary exposure method provided by JIS L 0841; circles indicate the test pieces having a value something of the order of 3; and crosses indicate the test pieces having a value below 3.

INDUSTRIAL APPLICABILITY

The heat transfer sheets of the present invention find wide applications as imaging materials in heat transfer systems with thermal heads.

We claim:

1. A heat transfer sheet comprising a substrate sheet and a dye carrying layer formed on its major side, characterized in that a dye included in said dye carrying layer is expressed by the following general formula (II):

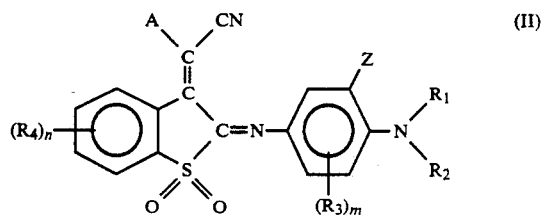

wherein:

A stands for a cyano, alkoxycarbonyl, aryloxycarbonyl, carbamoyl, alkylcarbamoyl, arylcarbamoyl, alkylcarbonyl, arylcarbonyl, alkylsulfonyl, alkylsulfonylamino, arylsulfonyl or aryl group, $R_1$ denotes a substituted or unsubstituted alkyl, aralkyl or aryl group, or an atom or atomic group which form a five- or six-membered ring together with Z, $R_2$ indicates a substituted or unsubstituted alkyl, aralkyl or aryl group, said $R_1$ and $R_2$ may form a five- or six-membered ring which may include an oxygen or nitrogen atom, $R_3$ stands for a hydrogen or halogen atom or an alkyl, alkoxy or acylamino group which may include a substituent, $R_4$ denotes a hydrogen or halogen atom or an alkyl, alkoxy, nitro, cyano, acylamino or aryl group which may include a substituent, Z indicates a hydrogen atom or an atom or atomic group which forms a five- or six-membered ring together with $R_1$, and n and m each are 1 or 2.

2. A heat transfer sheet as recited in claim 1, wherein said dye has a molecular weight of at least 400.

3. A heat transfer sheet as recited in claim 1, wherein Z is a hydrogen atom, $R_1$ and/or $R_2$ are an ethyl group which may contain a hydroxyl group, $R_3$ is an alkyl or alkoxyl group located at the ortho-position with respect to the azomethyne group, $R_4$ is a hydrogen atom, A is a cyano or alkoxycarbonyl group, and m and n each are 1.

4. A heat transfer sheet as recited in claim 1, wherein at least one of said substituents $R_1$–$R_3$ and A contains a polar group such as a hydroxyl, amino, alkylamino, acylamino, sulfonylamino, aminocarbonyl, aminosulfonyl, alkoxycarbonyl, alkoxysulfonyl, cyano, alkoxy, phenyl, cycloalkyl or nitro group or a halogen atom.

* * * * *